United States Patent [19]

Huet de Barochez et al.

[11] Patent Number: 5,888,542
[45] Date of Patent: Mar. 30, 1999

[54] MATRIX TABLET ALLOWING THE PROLONGED RELEASE OF THE SODIUM SALT OF TIANEPTINE AFTER ADMINISTRATION BY THE ORAL ROUTE

[75] Inventors: Bruno Huet de Barochez, Ingre; Patrick Wüthrich, Orleans, both of France

[73] Assignee: Adir Et Compagnie, Courbevoie, France

[21] Appl. No.: 844,942

[22] Filed: Apr. 23, 1997

[30] Foreign Application Priority Data

Apr. 24, 1996 [FR] France .................................. 96 05174

[51] Int. Cl.$^6$ ................ A61K 9/20; A61K 9/22; A61K 9/36

[52] U.S. Cl. ............ 424/464; 424/468; 424/480; 424/484

[58] Field of Search ................. 424/464, 468, 424/480, 484, 485, 486, 488

[56] References Cited

U.S. PATENT DOCUMENTS 5,446,070  8/1995  Mantelle ........................... 514/772.6

Primary Examiner—Thurman K. Page
Assistant Examiner—Sharon Howard
Attorney, Agent, or Firm—The Firm of Gordon W. Hueschen

[57] ABSTRACT

The invention relates to a matrix tablet for the prolonged release of the sodium salt of tianeptine which ensures a continuous and uniform release of the active ingredient after administration by the oral route.

7 Claims, 6 Drawing Sheets

MATRIX TABLET ALLOWING THE PROLONGED RELEASE OF THE SODIUM SALT OF TIANEPTINE AFTER ADMINISTRATION BY THE ORAL ROUTE

The subject of the present invention is a matrix tablet allowing the prolonged release of the sodium salt of tianeptine, providing uniform and constant blood levels after absorption of the galenic form by the oral route.

The sodium salt of tianeptine, a compound of formula (I):

[Chemical structure of tianeptine sodium salt showing HN-connected chain with COONa group, tricyclic system with N-SO2, H3C, and Cl substituent]

is a tricyclic antidepressant. The molecule used for administration to man is the sodium salt.

The sodium salt of tianeptine was up until now administered by the oral route in the form of immediate-release tablets containing 12.5 mg doses. The usual average prescription is three doses per day.

However, an immediate-release form may lead, in some subjects, to high blood peaks being obtained. A prolonged-release form makes it possible to avoid these blood peaks and to obtain a uniform blood concentration in man. This makes it possible to reduce the undesirable effects which may potentially occur by the "peak effect" accompanied by hydroelectrolytic- and metabolite-type disorders linked to the variations in the plasma levels of the active ingredient.

A prolonged-release form of the sodium salt of tianeptine therefore makes it possible to ensure a better therapeutic index in the treatment of anxiety and depression.

To do this, it is necessary to ensure a prolonged release over time, in a perfectly controlled manner. The rate of release should be reproducible and correlated with the blood concentrations observed after administration.

Among the mechanisms which may be called into play for controlling the diffusion of a soluble active ingredient, a major one may be picked out therefrom, which is the diffusion of the active ingredient through a gel formed after swelling of a hydrophilic polymer brought into contact with the dissolution liquid (in vitro), or with the gastrointestinal fluid (in vivo).

Numerous polymers have been described as being capable of allowing the formation of this gel. The major ones are the cellulose derivatives, in particular the cellulose ethers such as hydroxypropylcellulose, hydroxymethylcellulose, methylcellulose, methylhydroxypropylcellulose, and among the different commercial grades of these ethers those having fairly high viscosities. It should be noted that the systems described theoretically do not make it possible to obtain a zero order in the kinetics of release equation.

The manufacturing processes commonly used for the manufacture of such matrix tablets are either direct compression, after mixing the different excipients and the active ingredient(s), or wet granulation.

The matrix tablet described in the present invention combines, in an original manner, a polymer derived from cellulose and a calcium salt, this combination making it possible to obtain a perfectly controlled release of the active ingredient. In addition, this combination is perfectly suited to the physicochemical characteristics of the sodium salt of tianeptine.

This controlled release is practically linear for more than eight hours and is such that 50 percent of the total quantity of the sodium salt of tianeptine is released between 5 and 14 hours. Moreover, the matrix tablet according to the invention makes it possible to obtain a prolonged release of tianeptine leading to blood levels in man of between 50 and 300 ng/ml, 24 hours at most after administration of the tablet. The unit dosage may thus vary according to the age and the weight of the patient, the nature and the seriousness of the condition. In general, it ranges between 12.5 and 50 mg for a daily treatment.

The polymer used is a methylhydroxypropylcellulose of high viscosity, the inorganic salt is calcium hydrogen phosphate dihydrate. The combination of these two compounds makes it possible to obtain perfect control of the kinetics of release. The percentage of polymer derived from the cellulose is between 30 and 50% of the total mass of the tablet, the percentage of inorganic salt is between 10 and 60% of the total mass of the tablet. Various excipients may also be added for finishing the tablet.

The present invention also relates to the preparation of this matrix tablet. A wet granulation is carried out with the active ingredient, the inorganic salt and lactose, in order to create around the active ingredient a hydrophilic environment favorable to the good dissolution thereof, and also so as to obtain the most uniform possible unit dose. However, the addition of a binder is not necessary in this formulation in order to obtain a uniform tablet. After this granulation stage, a direct compression mixture is produced and then tableted.

BRIEF DESCRIPTION OF THE DRAWINGS

Reference is now made to the Figures of the drawings for a better understanding of the invention, wherein.

Figure 1:
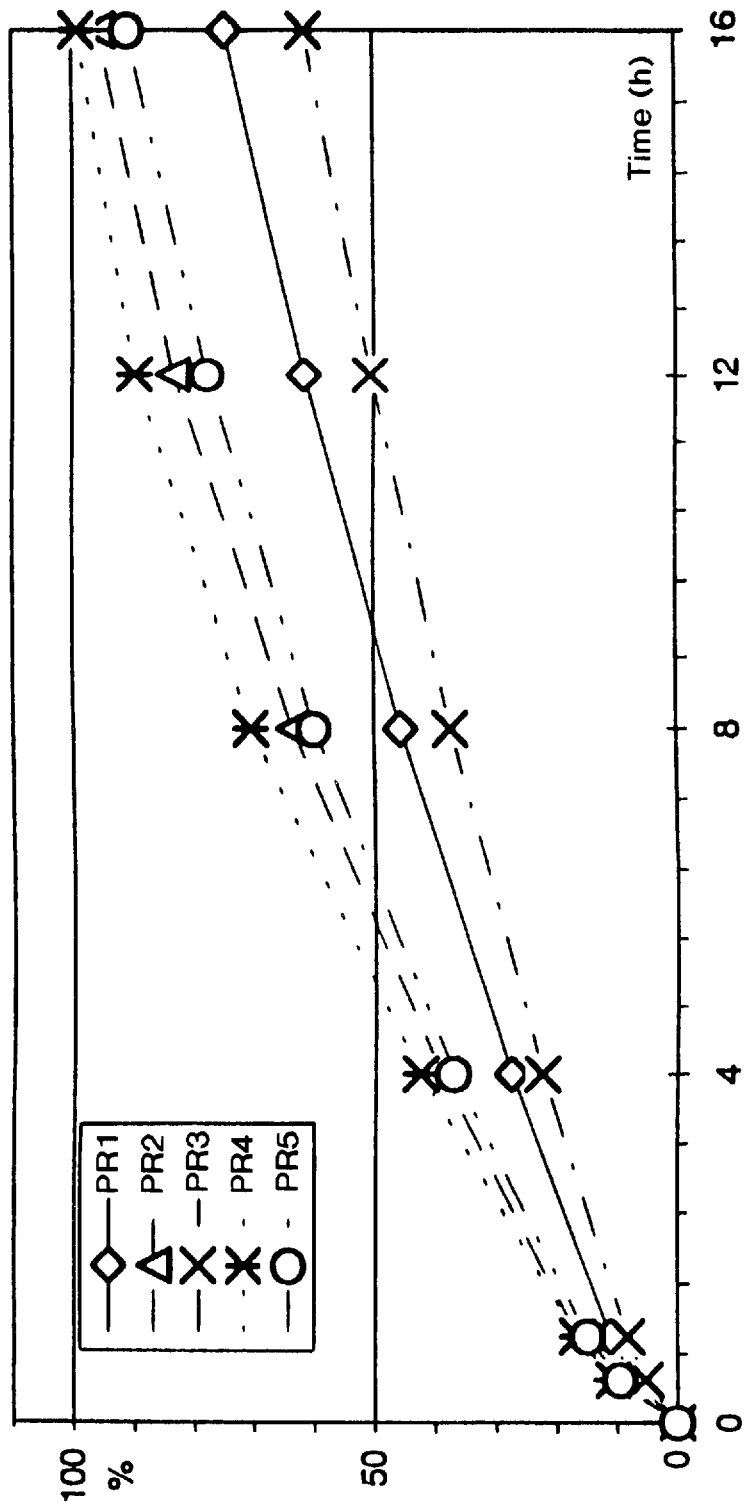
FIG. 1 is a graph showing the kinetics of dissolution in vitro of the batches PR1 to PR5 as set forth in Table 1, plotting percent dissolution against time in hours.

The following examples illustrate the invention but do not limit it in any manner. The preparation of the prolonged-release tablets is carried out according to the following manufacturing process:

Stage A

Mixing the sodium salt of tianeptine, calcium hydrogen phosphate dihydrate and lactose, then wetting this mixture with purified water or an aqueous-alcoholic solution. The wet mass prepared is then granulated, dried and then sized, so as to obtain a granule whose physical characteristics allow good filling of the matrices of a rapid tableting machine.

Stage B

Mixing the granule obtained in stage A with methylhydroxypropylcellulose.

Stage C

Lubricating the mixture obtained in stage B with colloidal silica and magnesium stearate.

Stage D

Compressing the lubricated mixture obtained in stage C on a rotary tableting machine, so as to obtain tablets having a hardness, measured by diametral crushing, of about 6 to 12 daN.

EXAMPLE 1

Example 1 shows the influence of the constituents on the kinetics of in vitro release. An experimental plan is used in which the quantity of methylhydroxypropylcellulose varies from 80 to 120 mg per tablet, the quantity of calcium hydrogen phosphate dihydrate from 0 to 146.4 mg per tablet and the quantity of lactose from 146.4 to 0 mg per tablet. The total quantity of diluent (lactose+calcium hydrogen phosphate dihydrate) is 146.4 mg per tablet.

The manufacture is carried out according to the operating procedure described in stages A to D.

TABLE 1

Formulas used for the optimization of the formulation, in mg per tablet

| | Batches | | | | | |
|---|---|---|---|---|---|---|
| Components | PR1 | PR2 | PR3 | PR4 | PR5 | PR6 |
| Tianeptine, Na salt | 50 | 50 | 50 | 50 | 50 | 50 |
| Lactose | 0 | 0 | 0 | 146.4 | 146.4 | 146.4 |
| Calcium hydrogen phosphate dihydrate | 146.4 | 146.4 | 146.4 | 0 | 0 | 0 |
| Methylhydroxypropylcellulose | 100 | 80 | 120 | 100 | 80 | 120 |
| Mg stearate | 3 | 3 | 3 | 3 | 3 | 3 |
| Colloidal silica | 0.6 | 0.6 | 0.6 | 0.6 | 0.6 | 0.6 |
| Final mass | 300 | 280 | 320 | 300 | 280 | 320 |

| | Batches | | | | |
|---|---|---|---|---|---|
| Components | PR7 | PR8 | PR9 | PR10 | PR11 |
| Tianeptine, Na salt | 50 | 50 | 50 | 50 | 50 |
| Lactose | 73.2 | 73.2 | 73.2 | 50 | 96.4 |
| Calcium hydrogen phosphate dihydrate | 73.2 | 73.2 | 73.2 | 96.4 | |
| Methylhydroxypropylcellulose | 100 | 80 | 120 | 100 | 100 |
| Mg stearate | 3 | 3 | 3 | 3 | 3 |
| Colloidal silica | 0.6 | 0.6 | 0.6 | 0.6 | 0.6 |
| Final mass | 300 | 280 | 320 | 300 | 300 |

Table 2 shows the percentages of active ingredient dissolved at 8 h as a function of the formulations used.

TABLE 2

Characteristics of the tablets

| | Batches | | | | | |
|---|---|---|---|---|---|---|
| Parameters | PR1 | PR2 | PR3 | PR4 | PR5 | PR6 |
| Mass (mg) | 299 | 300 | 302 | 280 | 320 | 280 |
| Active ingredient dissolved at 8 h (%) | 49 | 64 | 37 | 71 | 60 | 43 |

TABLE 2-continued

Characteristics of the tablets

| | Batches | | | | |
|---|---|---|---|---|---|
| Parameters | PR7 | PR8 | PR9 | PR10 | PR11 |
| Mass (mg) | 320 | 301 | 280 | 320 | 300 |
| Hardness (daN) | 9.0 | 8.9 | 9.0 | 9.0 | 9.5 |
| Active ingredient dissolved at 8 h (%) | 40 | 49 | 51 | 44 | 44 |

Figure 2:
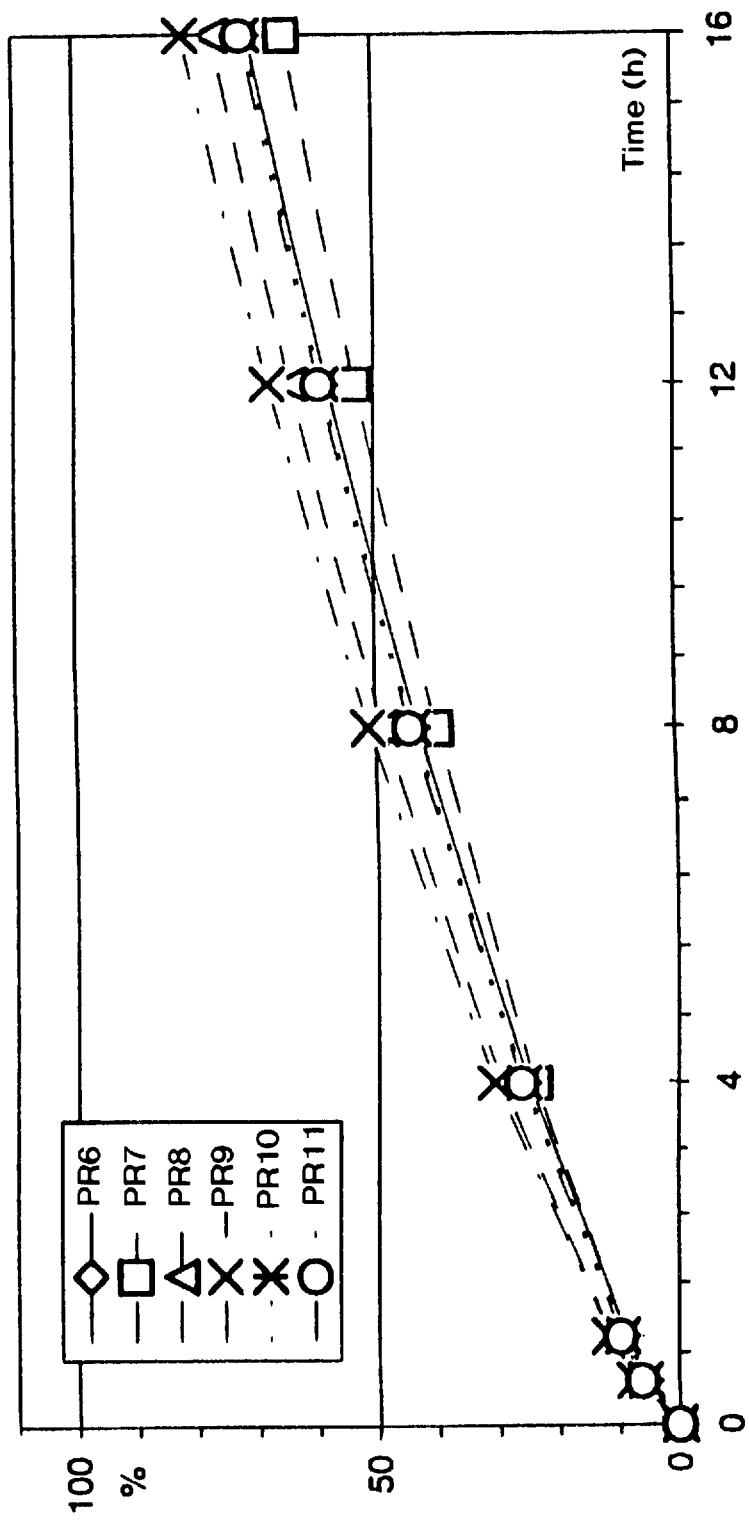
FIG. 2 is a graph showing the kinetics of dissolution in vitro of the batches PR6 to PR11 as set forth in Table 1, plotting percent dissolution against time in hours.

In FIGS. 1 and 2 are represented the curves of kinetics of dissolution for the different formulations used.

These curves show clearly that the percentages of methylhydroxypropylcellulose and calcium hydrogen phosphate dihydrate play an important role in the control of the kinetics of dissolution in vitro. The increase in methylhydroxypropylcellulose from 80 to 120 mg reduces the percentage of active ingredient dissolved at 8 h by about 7. Total substitution of the lactose by calcium hydrogen phosphate dihydrate reduces this same percentage by nearly 25.

EXAMPLE 2

A prolonged-release tablet (PR12) is prepared using the formula given in Table 3, according to the operating procedure described in stages A to D.

TABLE 3

Unit formula of the PR12 tablet

| Constituents | Quantities (mg) |
|---|---|
| Tianeptine sodium salt | 50 |
| Calcium hydrogen phosphate dihydrate | 50 |
| Lactose monohydrate | 96.4 |
| Methylhydroxypropylcellulose | 100 |
| Anhydrous colloidal silica | 0.6 |
| Magnesium stearate | 3 |
| White coating | 15 |

Figure 3:
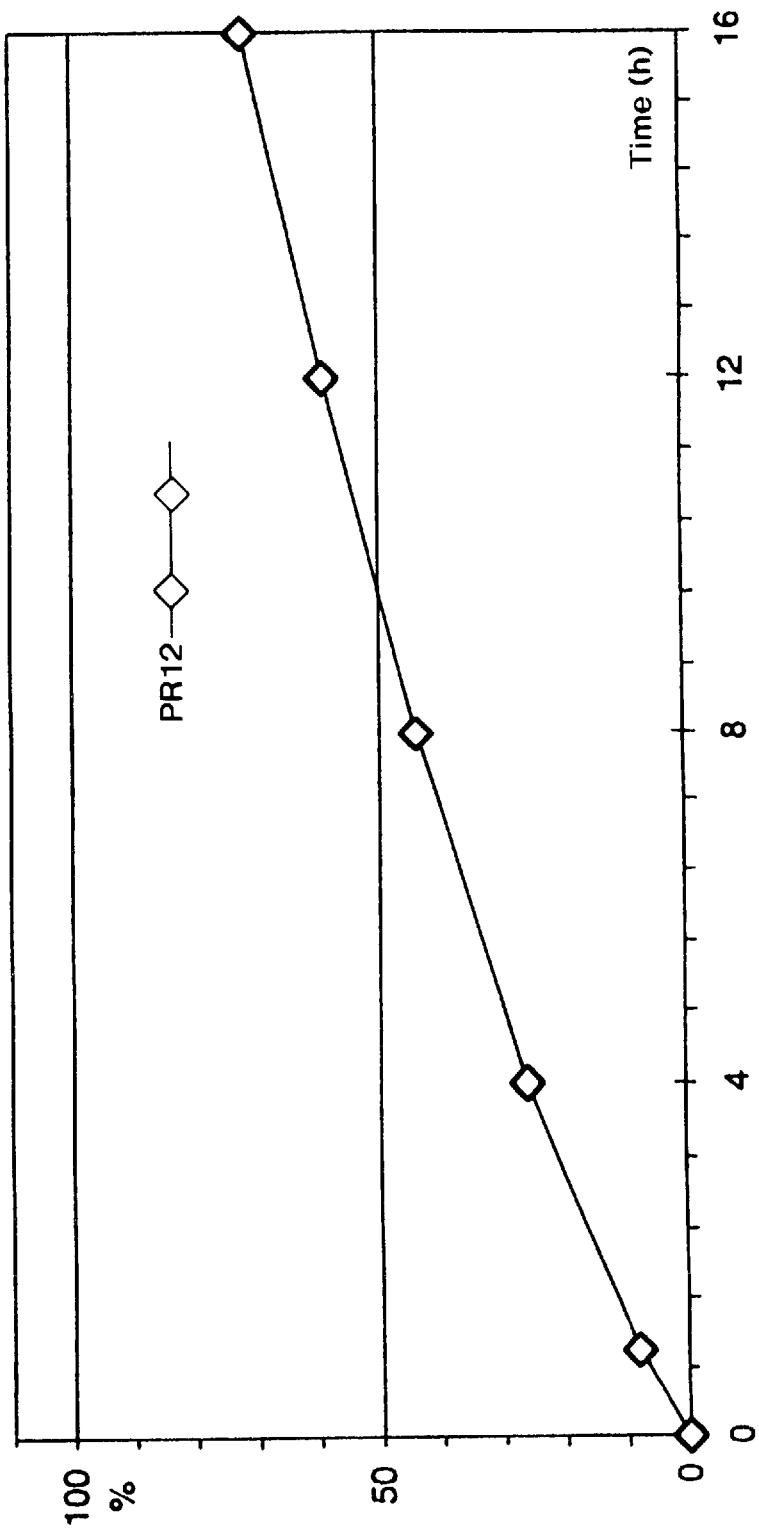
FIG. 3 is a graph showing the profile of in vitro dissolution of the PR12 form as set forth in Table 3, plotting percent dissolution against time in hours.

The profile of in vitro dissolution of this form (PR12) is presented in FIG. 3.

The plasma tianeptine sodium salt kinetics is measured in four subjects after a single administration of one PR12 tablet. The mean plasma concentration is given in FIG 4.

Figure 4:
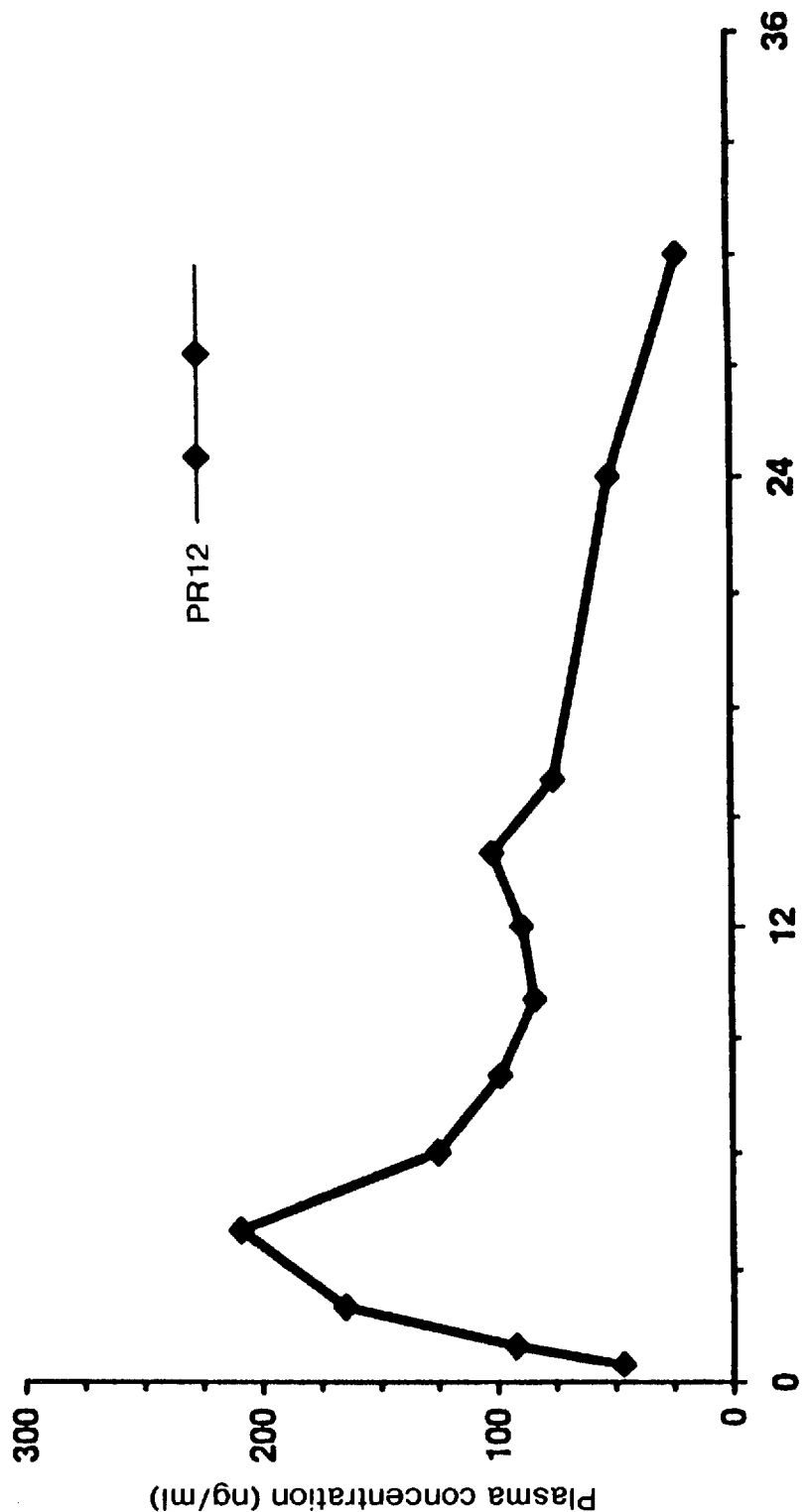
FIG. 4 is a graph of a mean curve showing the plasma Tianeptine kinetics after administration of a PR12 form to four healthy volunteers as a single administration, plotting plasma concentration in ng/ml against time in hours.

This curve of FIG. 4 shows a matrix-type dissolution profile (continuous release of the active ingredient), with a two-phase plasma kinetics (two plasma peaks).

EXAMPLE 3

Two prolonged-release tablets PR13 and PR14 are prepared using the formula given in Table 4, following the operating procedure described in Stages A to D. Two grades of methylhydroxypropylcellulose are used so as to prepare a slow-dissolution batch and a more-rapid-dissolution batch.

TABLE 4

Unit formula of the tablets PR13 and PR14

| Constituents | Tablet PR13 (mg) | Tablet PR14 (mg) |
|---|---|---|
| Tianeptine sodium salt | 50 | 50 |
| Calcium hydrogen phosphate dihydrate | 74 | 74 |
| Lactose monohydrate | 74 | 74 |
| Methylhydroxypropylcellulose 2208 40 Ps | 100 | 82 |

TABLE 4-continued

Unit formula of the tablets PR13 and PR14

| Constituents | Tablet PR13 (mg) | Tablet PR14 (mg) |
|---|---|---|
| Methylhydroxypropylcellulose 2208 1 Ps | 0 | 18 |
| Anhydrous colloidal silica | 0.5 | 0.5 |
| Magnesium stearate | 1.5 | 1.5 |
| White coating | 5 | 5 |

Figure 5:
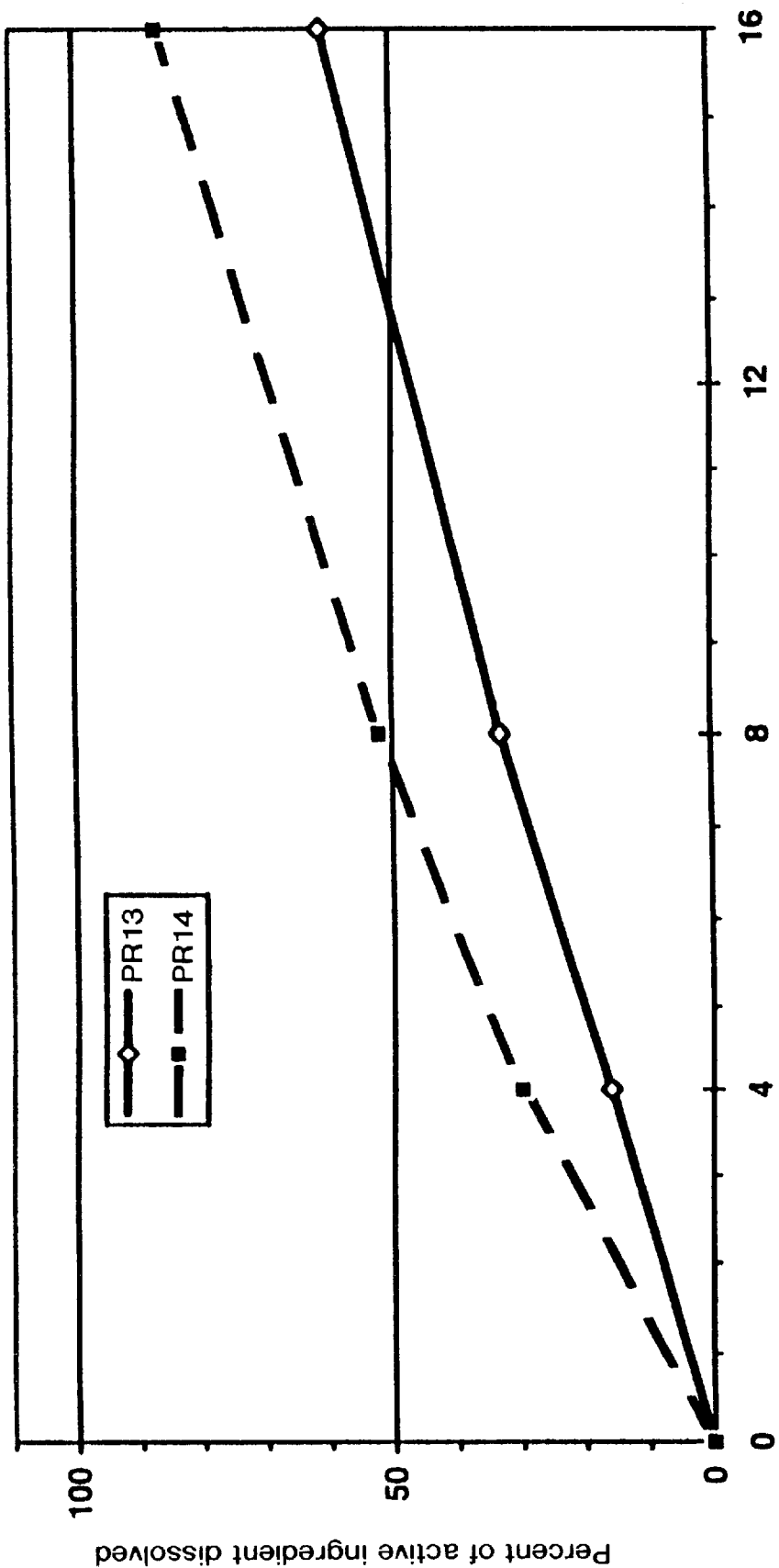
FIG. 5 is a graph showing the kinetics of in vitro dissolution of the PR13 and PR14 forms as set forth in Table 4, plotting percent of active ingredient dissolved against time in hours.

The profile of in vitro dissolution of this form is presented in FIG. 5.

Figure 6:
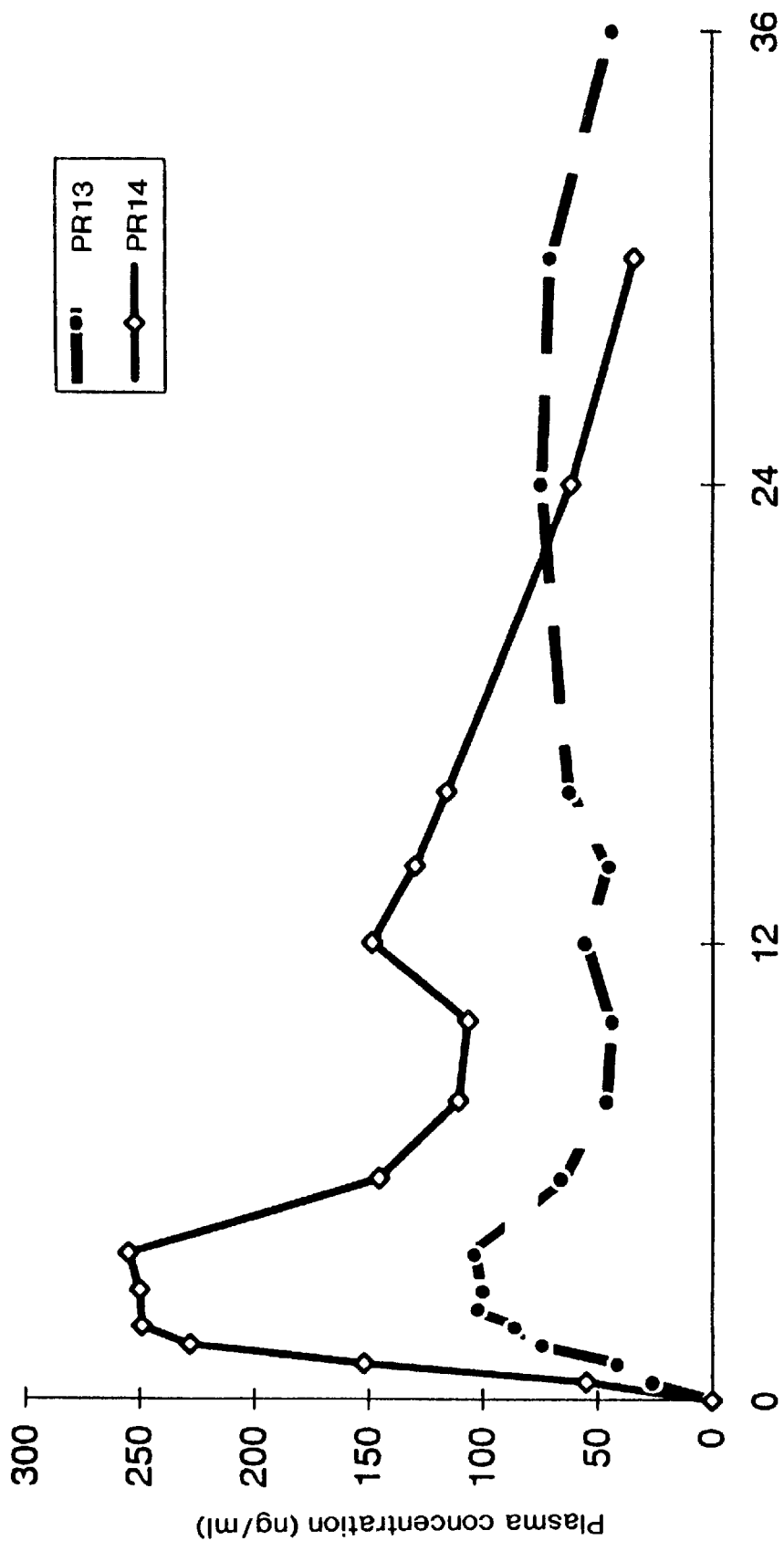
FIG. 6 is a graph showing plasma concentrations obtained after administration of the PR13 tablet or of the PR14 tablet in a crossover test, plotting the plasma concentration of active ingredient in ng/ml against time in hours.

The plasma tianeptine sodium salt kinetics is measured in eight subjects after a single administration of a PR13 or PR14 tablet in crossover. The mean plasma concentration is given in FIG. 6.

The comparison between the formulas PR13 and PR14 differing only in the grade of methylhydroxypropylcellulose used shows that the kinetics of in vitro dissolution of tianeptine sodium salt can also be controlled by this means. The relationship with the blood kinetics measured in vivo is very good. The two blood kinetics are significantly different. The two active ingredient release peaks are observed.

We claim:

1. A matrix tablet for the prolonged release of the sodium salt of tianeptine, wherein this prolonged release is controlled by the use of a polymer derived from cellulose and of a calcium salt.

2. The tianeptine matrix tablet as claimed in claim 1, wherein the polymer derived from cellulose is a methylhydroxypropylcellulose.

3. The tianeptine matrix tablet as claimed in claim 1, wherein the calcium salt is calcium hydrogen phosphate dihydrate.

4. The tianeptine matrix tablet as claimed in claim 1, wherein the percentages of cellulose derivative and of calcium salt are between 30 and 50% and between 10 and 60% of the total mass of the tablet, respectively.

5. The tianeptine matrix tablet as claimed in claim 1, wherein the percentages of cellulose derivative and of calcium salt allow a prolonged release of tianeptine leading to blood levels in man of between 50 and 300 ng/ml, 24 hours at most after administration of the tablet by the oral route.

6. A process for the preparation of the tianeptine matrix tablet as claimed in claim 1, wherein both a wet granulation and direct compression technique is used which comprises the following stages:

stage A: mixing the sodium salt of tianeptine, calcium hydrogen phosphate dihydrate and lactose, then wetting this mixture with purified water or an aqueous-alcoholic solution, the wet mass prepared is then granulated, dried and then sized, so as to obtain a granule whose physical characteristics allow good filling of the matrices of a rapid tableting machine, stage B: mixing the granule obtained in stage A with methylhydroxypropylcellulose, stage C: lubricating the mixture obtained in stage B with colloidal silica and magnesium stearate, stage D: compressing the lubricated mixture obtained in stage C on a rotary tableting machine, so as to obtain tablets having a hardness, measured by diametral crushing, of about 6 to 12 daN.

7. The tianeptine matrix tablet as claimed in claim 1, useful in the treatment of depression.

* * * * *